United States Patent

Smetana et al.

[11] Patent Number: 5,885,551
[45] Date of Patent: Mar. 23, 1999

[54] TREATMENT FOR DENTINAL HYPERSENSITIVITY

[76] Inventors: Alfred J. Smetana, 9 Larkspur Rd., Wayne, N.J. 07470; Jon Hayes, 9 Charter Ct., East Brunswick, N.J. 08816; Kuo-Chen Yeh, 210 Golf Edge, Westfield, N.J. 07090; Laura McCulloch, 18 Hampton Ct., Basking Ridge, N.J. 07920

[21] Appl. No.: 904,984

[22] Filed: Aug. 1, 1997

[51] Int. Cl.⁶ .............................. A61K 7/16; A61K 6/02; A61K 6/097; A61K 7/26
[52] U.S. Cl. .............................. 424/49; 424/48; 424/435; 424/440; 424/448
[58] Field of Search .................................. 424/48, 49–58, 424/435, 440, 448, 449

[56] References Cited

U.S. PATENT DOCUMENTS

| | | | |
|---|---|---|---|
| 3,699,221 | 10/1972 | Schole et al. | 424/54 |
| 3,863,006 | 1/1975 | Hodosh | 424/49 |
| 3,888,976 | 6/1975 | Mlkvy et al. | 424/44 |
| 3,988,434 | 10/1976 | Schole et al. | 424/54 |
| 4,057,621 | 11/1977 | Pashley et al. | 424/49 |
| 4,146,606 | 3/1979 | Yamaga et al. | 424/52 |
| 4,401,648 | 8/1983 | Piechota | 424/49 |
| 4,645,662 | 2/1987 | Nakashima et al. | 424/52 |
| 4,775,525 | 10/1988 | Pera | 424/50 |
| 4,855,128 | 8/1989 | Lynch et al. | 424/49 |
| 5,188,818 | 2/1993 | Merianos et al. | 424/49 |
| 5,234,971 | 8/1993 | Imai et al. | 433/228.1 |
| 5,240,697 | 8/1993 | Norfleet et al. | 424/52 |
| 5,244,651 | 9/1993 | Kayane et al. | 424/57 |
| 5,270,031 | 12/1993 | Lim et al. | 424/49 |
| 5,374,417 | 12/1994 | Norfleet et al. | 424/49 |
| 5,403,577 | 4/1995 | Friedman | 424/49 |
| 5,510,102 | 4/1996 | Cochrum | 424/78.08 |
| 5,589,159 | 12/1996 | MarKowitz et al. | 424/49 |
| 5,597,552 | 1/1997 | Herms et al. | 424/49 |
| 5,614,204 | 3/1997 | Cochrum | 424/78.08 |
| 5,645,853 | 7/1997 | Winston et al. | 424/440 |
| 5,653,964 | 8/1997 | Herms et al. | 424/49 |
| 5,693,314 | 12/1997 | Campbell et al. | 424/49 |
| 5,718,885 | 2/1998 | Onsold et al. | 424/49 |
| 5,792,446 | 8/1998 | Ashley | 424/52 |

OTHER PUBLICATIONS

Tung et al "Characterization and Modification of Electrochemical Properties of Teeth" J. Dent. Res. 62 (1) 60–64, Jan. 1983.

*Primary Examiner*—Shep K. Rose
*Attorney, Agent, or Firm*—Ostrolenk, Faber, Gerb & Soffen, LLP

[57] ABSTRACT

A method for treating dentinal hypersensitivity by administering a therapeutic amount of an alginate to a hypersensitive tooth.

12 Claims, No Drawings

TREATMENT FOR DENTINAL HYPERSENSITIVITY

BACKGROUND OF THE INVENTION

1. Field of the Invention

The invention is directed to formulations for treating hypersensitive teeth and to methods for making and using such formulations.

2. Description of Related Art

Hypersensitive teeth can cause pain and discomfort when subjected to changes in temperature, pressure or chemical action. Exposure of the dentin frequently leads to hypersensitivity. Dentin exposure may occur due to recession of the gums, periodontal disease or improper dental care.

A significant breakthrough in the treatment of hypersensitivity came with U.S. Pat. No. 3,122,483 to Rosenthal. This patent reported that certain strontium compounds, especially strontium chloride, acted as desensitizing agents. Later, U.S. Pat. No. 3,863,006 to Hodosh reported that potassium nitrate could act as a desensitizer, and U.S. Pat. No. 4,631,186 and U.S. Pat. No. 4,751,072, both to Kim, reported that potassium chloride and potassium bicarbonate were also satisfactory desensitizers.

Ionic salt desensitizers, such as potassium nitrate and strontium chloride, appear to act by penetrating hypersensitive teeth through "tubules" in the dentin of the tooth. Dentinal tubules are small open tubes in the dentin that facilitate energy and material transfer between the interior and exterior of the tooth. The ionic desensitizers apparently interfere with the operation of the nerve in the tooth, reducing the nerve activity, and thereby reducing the sensitivity of the tooth.

Examples of ionic salts as desensitizers also include U.S. Pat. No. 3,699,221 to Schole et al., issued Oct. 17, 1972. This patent is directed to an early system for desensitizing teeth. The patent is directed to a strontium chelate in dentifrice, tooth powder, or chewing gum form. (A number of ingredients are listed in the toothpaste formulation, including 1% by weight "algin" in two examples. The purpose of the algin is not made clear.)

While the desensitizing properties of ionic desensitizers are excellent, such desensitizers are not "permanent," in that they do not remain in proximity to the tooth nerve forever, and the desensitizer must be reapplied to the tooth continually. In an effort to sustain the administration of an ionic desensitizing salt to the tooth, U.S. Pat. No. 5,188,818 to Merianos et al., issued Feb. 23, 1993, described a strontium salt of a maleic anhydride-methyl vinyl ether copolymer as a desensitizer. The polymer apparently adheres to teeth and releases the strontium over time.

A second class of desensitizing materials has recently been developed. This class of desensitizers acts to occlude or otherwise seal off some or all of the tubules present in the dentin and so reduce material and energy exchange between the interior and exterior of the tooth. These materials may have more or less affinity for the material in the dentin tubule and may exhibit more or less permanence as an occluding agent. Some materials migrate to the tubule quickly and are very prompt in occluding tubules, while other materials take time to develop as occluding agents. The materials may also remain in the tubules for varying amounts of time. Thus, the degree of occlusion of the many tubules found in dentin and the rapidity of the onset and the rate of decline of meaningful occlusion are important aspects of such occluding agents.

An example of an occluding agent is found in U.S. Pat. No. 5,270,031 to Lim et al., issued Dec. 14, 1993. This patent is directed to a tubule occluding desensitizer comprising a polyacrylic acid such as Carbopol® polymeric materials (B.F. Goodrich). Another tubule occluding composition is disclosed in U.S. Pat. No. 5,374,417 to Norfleet et al., issued Dec. 20, 1994. That patent discloses a potassium salt of a synthetic anionic polymer, such as a polycarboxylate.

One important aspect of desensitizing agents, whether ionic salts or tubule occluding agents, is that the agent must not be toxic or otherwise harmful to persons being treated for hypersensitivity. Preferably, a good desensitizing agent should be compatible with other oral care ingredients, such as conventional dentifrice or mouthwash ingredients, so that the agent may be administered in a conjunction with other dental therapies and prophylaxis. The organoleptic qualities of the desensitizing agent should also be pleasant to encourage compliance.

Although alginates have been known for some time as binders in dentifrice applications, we have now discovered that alginate salts are excellent occluding agents and meet all the requirements for a good desensitizing agent.

Alginates are salts of alginic acid, a polysaccharide having a molecular weight of about 240,000 daltons. The polysaccharide is extracted from giant brown seaweed and kelp. Alginic acid has been described as a linear polymer of $\beta$-(1-4)-D-mannosyluronic acid and $\alpha$-(1-4)-L-gulosyluronic acid residues. The exact proportion of the monomers depends on the source of the polymer. The salts, typically sodium salts, of the acid are used as gelling agents and as thickeners in dentifrice applications and ice cream.

The use of alginate in a dentifrice system is demonstrated in U.S. Pat. No. 4,401,648 to Piechota. Jr., issued Aug. 30, 1983. This patent is directed to a dental creme containing a gel system of xanthan and alginate. The ratio of xanthan and alginate in the system is 1:3 to 3:1 and the system comprises 0.2–5% of the dental creme.

Alginates have also been used in conjunction with anti-caries agents as in U.S. Pat. No. 4,775,525 to Pera, issued Oct. 4, 1988. That patent is directed to a composition for reducing dental plaque. The essential ingredient of the patent is a calcium ion chelating agent comprising sodium alginate. Although the patent is directed to caries control, the composition may also contain a desensitizing agent such as strontium chloride.

U.S. Pat. No. 4,855,128 to Lynch et al., issued Aug. 8, 1989, is directed to plaque inhibitory agents in mouthwashes, toothpastes and other oral care systems. These agents are present from about 0.0025% to about 2.000% on a weight to volume basis, and are polysaccharides selected from xanthan gum, gum tragacanth (pectin), guar gum, gum karaya, chondroitin sulfate, polygalacturinic acid, sodium alginate and carrageenans of the kappa/lambda configuration. These ingredients apparently inhibit the coaggregation of bacteria and so inhibit the formation of plaque.

Alginates have been used in dentifice formulations for other purposes as well. The permeability of the enamel surface of teeth was reported in Tung, M. S. and Brown, W. E., "Characterization and Modification of Electrochemical Properties of Teeth," J. Dent. Res. 62(1):60–64 (Jan. 1983). The article reported that the permeability of teeth could be modified by anionic compounds such as phytate and alginate and by cationic compounds such as protamine, polyarginine, and polylysine, or by an alternating coating of these compounds. The purpose of this study was to investigate the behavior of incipient caries, which was reported to form below the enamel surface.

Another occluding agent is found in U.S. Pat. No. 4,645,662 to Nakashima et al., issued Feb. 24, 1987. This patent is directed to an oral composition for treating dentinal hypersensitivity. The composition contains aluminum and a carboxylate compound which combine to form a composition that occludes the dentin tubules. Among the binders that may be used in a dentifrice containing the occluding compounds are: carrageenan, cellulose derivatives (e.g., sodium carboxymethylcellulose, methylcellulose, hydroxyalkylcelluloses and sodium carboxymethyl-hydroxyethyl cellulose), alkali metal alginates (e.g., sodium alginate), alginic acidpropylene glycol ester, gums (e.g., xanthan gum, tragacanth gum, karaya gum, and gum arabic), synthetic binders (e.g. polyvinyl alcohol, sodium polyacrylate, carboxy vinyl polymer, and polyvinyl pyrrolidone), and inorganic binders (e.g., gelling silica, gelling aluminum silica, magnesium aluminum silicate (sold under the trade name Veegum), and synthetic hectorite clays such as Laponite (trade name)). The binder is added in an amount of 0.1 to 10% by weight, and preferably 0.2–5% by weight. The only reported example using an alginate, however, used one percent alginate and obtained unacceptable results. (See Example 2 and formulation #4 in Table 5.)

Despite the presence of occluding agents and other desensitizing agents, the search continues for an occluding agent that has the proper mix of desensitizing and organoleptic qualities to provide a meaningful therapy for treatment and relief of hypersensitivity while maintaining a pleasing "mouth-feel" for the therapeutic product. Alginates have not heretofore been recognized as desensitizing agents, even in desensitizing formulations.

SUMMARY OF THE INVENTION

The principal object of the invention therefore is to provide an effective tubule blocking agent and an oral care composition having a high degree of effectiveness in treating and relieving dentinal hypersensitivity, a negligible degree of toxicity, and a high degree of patient acceptance.

It is a further object of the invention to provide methods of delivering the oral care composition to the affected tooth or teeth in a manner to encourage patient compliance with the hypersensitivity control regimen.

It is still another object of the invention to provide methods of preparing the oral care composition in such a manner that the resulting formulation is safe, effective, stable and suitable from an organoleptic aspect.

It is an advantage of the invention that the alginates are compatible with fluorides and other conventional dentifrice ingredients.

Additional objects and advantages of the invention will be set forth in part in the description that follows, and in part will be obvious from this description, or may be learned by practice of the invention. The objects and advantages of the invention may be realized and attained by means of the instrumentalities and combinations particularly pointed out in the appended claims.

To achieve the foregoing objects and in accordance with the purpose of the invention, as embodied and broadly described herein, the invention provides an oral care composition for treating dentinal hypersensitivity comprising an amount of alginate sufficient to treat hypersensitivity when used in a therapeutic regimen.

To further achieve the foregoing objects and in accordance with the purpose of the invention, the invention further provides a method for treating dentinal hypersensitivity by administering to the affected tooth or teeth of a patient having dentinal hypersensitivity an amount of alginate sufficient to treat hypersensitivity when used in a therapeutic regimen.

To further achieve the foregoing objects and in accordance with the purpose of the invention, the invention further provides a method for making a formulation for treating dentinal hypersensitivity by combining a therapeutic amount of alginate with a carrier.

While this specification concludes with claims particularly pointing out and distinctly claiming that which is regarded as the present invention, the objects and advantages of this invention may be more readily ascertained from the following description of the presently preferred embodiments.

DESCRIPTION OF THE PREFERRED EMBODIMENTS

Reference will now be made in detail to the presently preferred embodiments of the invention.

The invention comprises a composition containing alginic acid or a derivative thereof for the treatment of dentinal hypersensitivity by application of the composition to teeth via a vehicle such as a dentifrice, mouth rinse, lozenge or chewing gum.

Alginic acid derivatives have long been known in dental applications as a binders, plaque inhibition agents or zinc ion complexing agents to improve associated organoleptic properties. Such derivatives, called alginates herein, include alginic acid itself and salts thereof, preferably alkali alginates and most preferably sodium alginate, potassium alginate, propylene glycol alginates, and ammonium alginates. Other known applications include use as a nontoxic bulking agent in food and a discrete single dosage unit for applications including mouthwash and chewable toothpaste.

The alginate should preferably be combined with a delivery system such as a dentifrice, mouth rinse or mouthwash, creme, lotion, oral gel, wipe or other known oral care delivery system for topical administration to teeth. While an alginate itself will act as a desensitizing agent without a carrier, direct delivery of the alginate is not favored for organoleptic reasons.

Desensitizing alginates may also be delivered in a dentifrice vehicle comprising alginate, abrasive, humectant, flavor, sweetener, detergent, other binders if required, and a fluoridating source if desired. Additional desensitizers, such as strontium and potassium compounds may also be included, but the presence of such additional ionic desensitizers is not expressly preferred at present. Alginates act as tubule occluders that may interfere with the migration of the nerve agents through the tubules. Alternatively, alginates may actually carry desensitizing ions into the tubules and then release the ionic desensitizing agents in the tubule.

Alginates can be used in a mouth rinse with humectant, sweetener, flavor, detergent and other actives as desired, such as anti-caries agents or antimicrobial agents. In a chewing gum alginates may be combined with other binders if required, humectant, sweetener, flavor and dye. Alginates may be used in a lozenge vehicle comprising humectant, sweetener, flavor and dye.

The relative weight percentage of alginate in any delivery system is, of course, a function of the dosage of the alginate and the dosage of the delivery system and the amount of time the delivery system stays in contact with the affected site. In dentifrices, for example, the alginate preferably comprises from about 0.01% to at least about 10% w/w of the dentifrice. Below about 0.01% by weight, the efficacy of the alginate is difficult to perceive, and above about 10% by weight little marginal efficacy is observed. Other than the organoleptic qualities of the dentifrice and the desirability of other dentifrice ingredients, however, there is no reason that a dentifrice could not contain more than 10% by weight alginates.

While a dentifrice containing the alginate may comprise no less than about 0.01% alginate by weight, the dentifrice should preferably contain no less than about 0.02% alginate, more preferably no less than about 0.5% alginate and even more preferably no less than about 1% alginate by weight. More preferably, the alginate should comprise no less than about 2% by weight of the dentifrice, and most preferably the alginate should comprise at least about 5% by weight of the dentifrice.

While a dentifrice containing the alginate may comprise more than 10% by weight alginate, there is little point in such a formulation as little additional occlusion occurs. Other ingredients are generally included in a dentifrice formulation that might suffer from excess alginate. More preferably, a dentifrice containing the alginate should comprise no more than about 8% by weight alginate, and even more preferably, no more than about 7% by weight alginate. As stated above, most preferably, the alginate should comprise about 5% by weight of the dentifrice composition.

A further possible benefit of alginate in oral care compositions such as dentifrices, is that the alginate may play a dual role of desensitizer and binder.

The process for making an alginate desensitizing formulation in accordance with the invention is to combine the ingredients for any conventional oral care delivery system with the alginate of the invention. The alginate may be added along with water or with any hydrophillic ingredient or ingredients in the preparation of the oral care delivery system through simple mixing.

The process for using an alginate desensitizing formulation in accordance with the invention is to use the oral care delivery system containing the desensitizing alginate. Thus, a patient should brush his or her teeth with the desensitizing dentifrice or rinse his or her mouth with a desensitizing alginate mouth rinse. The preferred embodiments of the invention will be set forth in more detail in the accompanying examples.

EXAMPLES 1–8

Prototype dentifrices containing sodium alginate were tested for tubule occlusion properties using an in-vitro model of dentin sensitivity first described by Pashley (J. Periodontology, Vol. 55, No. 9, p.522, September 1984). U.S. Pat. No. 5,270,031 to Lim et al., issued Dec. 14, 1993, also describes this methodology. Both references are incorporated herein by reference.

In this method, intact human molars free of caries or restorations were sectioned perpendicular to the long axis of the tooth with a metallurgical saw (and water lubrication) into thin disc sections about 0.6 to 0.8 mm thick. Sections containing only dentin and free of enamel were retained for testing. These sections were then etched with a EDTA (ethylenediamine tetra acetic acid) solution to remove the smear layer. The dentin discs were then mounted in a split chamber device as reported in Pashley, J. Dent. Research, 57:187 (1978). This special leak proof chamber was connected to a pressurized fluid reservoir containing a tissue culture fluid. By using a mixture of pressurized nitrogen and carbon dioxide gas, the fluid was maintained at physiological pH. To further simulate the intraoral condition, the disks were wetted with human saliva.

An air bubble was injected into a glass capillary tube mounted on a ruler or other measuring instrument, and the fluid in the capillary was placed in contact with the fluid behind the dentin disc. The bubble was displaced as fluid passed through the dentin tubules. By measuring the displacement of this bubble as a function of time, the fluid flow through the dentin disk was measured. (It has been reported that the fluid actually flows out of dentin tubules from the interior of a normal tooth.)

Following measurement of the baseline fluid flow in the dentin disk, the experimental mixture or dentifrice was applied to the external disk surface with a nylon brush. After a defined period of brushing, of about thirty seconds, the experimental material was rinsed off, and the post application hydraulic conductance was measured. In this fashion, the ability of alginates to obstruct fluid flow when used in a dentifrice was determined. The percent flow reduction induced by brushing with experimental materials was then calculated.

The dentin disc was then brushed for one minute with water and the fluid flow was measured. Finally, elevated back pressure was applied to the disc, and the tubules were "purged." The fluid flow was again measured. The purpose of this final test was to evaluate how tenaciously the tubule blocking agent (sodium alginate) maintained its effectiveness.

The formulation set forth in the tables was used to test the hydraulic conductance reducing abiligy of sodium alginate as a function of concentration. The sodium alginate selected was KELTONE LVCR®, a commercial product. The results are set in Tables 1 and 2.

TABLE 1

Formula Composition

| INGREDIENTS | WEIGHT PERCENT |
| --- | --- |
| Sodium Fluoride | 0.232 |
| Sodium Saccharin | 0.400 |
| Titanium Dioxide | 1.500 |
| Sorbitol Solution | 12.000 |
| Glycerin | 20.000 |
| Silicon Dioxide | 2.000 |
| Amorphous Silica | 10.000 |
| KELTONE LVCR (Sodium Alginate) | 0–7 |
| Sodium cocomethyl acid taurate | 1.500 |
| Flavor | 1.000 |
| Purified water | Q.S. to 100% |

TABLE 2

Fluid Flow Reduction of Examples 1–8

| Example | Wt. % Alginate | Post Brushing Fluid Flow Reduction | Post Rinsing Fluid Flow Reduction | Post Purging Fluid Flow Reduction |
| --- | --- | --- | --- | --- |
| 1 | 0% | 20.6% | 8.62% | 11.76% |
| 2 | 1% | 27.3% | 9.46% | 7.66% |
| 3 | 2% | 57.5% | 38.32% | 23.44% |
| 4 | 3% | 64.2% | 40.36% | 28.56% |
| 5 | 4% | 75.3% | 66.58% | 42.1% |
| 6 | 5% | 82.8% | 65.44% | 53.9% |
| 7 | 6% | 90.6% | 87.46% | 79.94% |
| 8 | 7% | 86.1% | 83.1% | 72.08% |

EXAMPLES 9–16

The following dentifrice formulations were prepared in the following manner. Purified water was added into a whipmixer mixer equipped with a vacuum system (a KORUMA mixer may be used for larger, i.e., pilot plant, batches). Key ingredients such as sodium fluoride and Triclosan, as appropriate, were added to the mixer, followed by sodium saccharin, titanium dioxide, and silicon dioxide.

The resulting bulk material was mixed for approximately 10–30 minutes (under vacuum) followed by the addition of abrasive, alginate (KELTONE LVCR), premix (humectant and gum), flavor and detergent. Final mixing of 20–30 minutes was conducted under vacuum to deaerate the product. The resulting dentifrices had the compositions set out below.

TABLE 3

Formulations of Examples 9–16

| Ingredient | Ex. 9 | Ex. 10 | Ex. 11 | Ex. 12 | Ex. 13 | Ex. 14 | Ex. 15 | Ex. 16 |
|---|---|---|---|---|---|---|---|---|
| Sodium MFP | 0.83 | — | — | — | 0.31 | — | — | — |
| Sodium Fluoride | — | 0.23 | 0.31 | 0.23 | — | 0.23 | 0.31 | 0.23 |
| Triclosan | — | — | 0.30 | — | 0.30 | — | 0.30 | — |
| Sorbitol Solution | 15.00 | 12.00 | 12.00 | 12.00 | 12:00 | 18.00 | 18.00 | 12.00 |
| Sodium Sacch. | 0.40 | 0.40 | 0.40 | 0.30 | 0.30 | 0.30 | 0.30 | 0.30 |
| Titanium Dioxide | 1.00 | 1.50 | 1.50 | 1.00 | 1.00 | 1.00 | 1.00 | 1.00 |
| AEROSIL 200 | 2.00 | 2.00 | 2.00 | — | — | — | — | — |
| Calcium Carb., Heavy | 18.00 | — | — | — | — | — | — | — |
| Glycerin | 12.00 | 20.00 | 20.00 | 10.00 | 10.00 | 10.00 | 10.00 | 10.00 |
| KELTONE HVCR | 2.40 | — | — | — | — | — | — | — |
| KELTONE LVCR | — | 5.00 | 5.00 | 5.00 | 5.00 | 5.00 | 5.00 | 4.50 |
| ZEODENT 165 | — | — | — | 4.00 | 4.00 | 3.00 | 3.00 | 4.00 |
| TIXOSIL 73 | — | 10.00 | 10.00 | 10.00 | 10.00 | 10.00 | 10.00 | 10.00 |
| TEGO-BETAINE ZF | — | — | — | 2.00 | 2.00 | 2.00 | 2.00 | 2.00 |
| IGEPON TC 42 | 1.50 | 1.50 | 1.50 | — | — | — | — | — |
| Flavor | 0.90 | 1.00 | 1.00 | 1.00 | 1.00 | 1.00 | 1.00 | 1.00 |
| Purified Water | Q.S. | Q.S. | Q.S. | Q.S. | Q.S. | Q.S. | Q.S. | Q.S. |

Several of the dentifrice formulations were evaluated for reduction of fluid flow. The results are set forth in Table 4.

TABLE 4

Flow Reduction for Certain Examples

| Ex. # | Principal Ingredients | % Flow Reduction |
|---|---|---|
| 9 | KELTONE HVCR (2.4%); Sodium MFP | 78% |
| 10 | KELTONE LVCR (5%); Sodium Fluoride (0.232%) | 83% |
| 15 | KELTONE LVCR (5%); Sodium Fluoride (0.31%); Triclosan (0.3%) | 94% |
| 16 | KELTONE LVCR (4.5%); Sodium Fluoride (0.232%) | 87% |

EXAMPLE 17

A lozenge for delivering the alginate comprised the following ingredients:

| Ingredient | % wt/wt |
|---|---|
| Citric Acid | 0.2 |
| Flavor and Color | 0.3 |
| Sorbitol Seed | 0.2 |
| Sodium Alginate | 5.0 |
| Neosorb | Q.S. to 100 |

EXAMPLE 18

To form a chewing gum, the following ingredients were mixed:

| Ingredient | % wt/wt |
|---|---|
| Chewing gum base (Dreyfus) | 24.0 |
| Hydrogenated starch hydrolysate | 11.5 |
| Sodium alginate | 3.0 |
| Water | 1.9 |
| Flavor color | 0.4 |
| Glycerin | 1.0 |
| Lecithin | 0.4 |
| Calcium saccharin | 0.1 |
| Sorbitol | Q.S. to 100 |

The purpose of the above description is to illustrate some embodiments of the present invention without implying a limitation. It will apparent to those skilled in the art that various modifications and variations may be made in the formulations and methods of the invention without departing from the scope or spirit of the invention.

What is claimed is:

1. In a method of desensitizing hypersensitive teeth by applying a desensitizing tubule occluding amount of an oral composition selected from the group consisting of dentifrice, mouthwash, gal, chewing gum,. lozenge and buccal adhesive patch, containing a desensitizing agent, the improvement comprising the step of occluding and thereby sealing the dentinal tubules in the dentine of the hypersensitive teeth with an effective tubular blocking amount of an alginate selected from the group consisting of alginic acid, potassium alginate, propylene glycol, alginate, sodium alginate and mixtures thereof as the essential tubular blocking agent and in the absence of additional strontium or potassium desensitizing agents.

2. The method of claim 1, wherein said alginate is alginic acid.

3. The method of claim 2, wherein said alginate is sodium alginate.

4. The method of claim 1, wherein said oral composition is a dentifrice and said alginate comprises from about 0.1% to about 10% by weight of said dentrifice.

5. The method of claim 4, wherein said alginate comprises from about 0.2% to about 10% by weight of said dentifrice.

6. The method of claim 5, wherein said alginate comprises from about 0.5% to about 10% by weight of said dentifrice.

7. The method of claim 6, wherein said alginate comprises from about 1% to about 10% by weight of said dentifrice.

8. The method of claim 7, wherein said alginate comprises from about 2% to about 8% by weight of said dentifrice.

9. The method of claim 8, wherein said alginate comprises from about 2% to about 7% by weight of said dentifrice.

10. The method of claim 9, wherein said alginate comprises about 5% by weight of said dentifrice.

11. The method of claim 4, wherein said alginate is sodium alginate.

12. The method of claim 7, wherein said alginate is sodium alginate.

* * * * *